United States Patent
Herrmann et al.

(10) Patent No.: US 7,652,145 B2
(45) Date of Patent: Jan. 26, 2010

(54) ALKYLIDENE COMPLEXES OF RUTHENIUM CONTAINING N-HETEROCYCLIC CARBENE LIGANDS; USE AS HIGHLY ACTIVE, SELECTIVE CATALYSTS FOR OLEFIN METATHESIS

(75) Inventors: Wolfgang Anton Herrmann, Freising (DE); Wolfgang Schattenmann, Burghausen (DE); Thomas Weskamp, Munich (DE)

(73) Assignee: Degussa AG (DE)

( * ) Notice: Subject to any disclaimer, the term of this patent is extended or adjusted under 35 U.S.C. 154(b) by 1329 days.

(21) Appl. No.: 11/021,967

(22) Filed: Dec. 23, 2004

(65) Prior Publication Data
US 2005/0107626 A1 May 19, 2005

Related U.S. Application Data

(62) Division of application No. 10/630,552, filed on Jul. 29, 2003, which is a division of application No. 09/647,742, filed as application No. PCT/EP99/01785 on Mar. 18, 1999, now Pat. No. 6,635,768.

(30) Foreign Application Priority Data
Apr. 6, 1998 (DE) .............................. 198 15 275.2

(51) Int. Cl.
C07F 15/00 (2006.01)
B01J 31/00 (2006.01)
C08F 4/80 (2006.01)

(52) U.S. Cl. ...................... 548/101; 548/262.2; 556/22; 556/136; 526/171; 502/155

(58) Field of Classification Search ................. 548/101, 548/262.2; 556/22, 136; 526/171; 502/155
See application file for complete search history.

(56) References Cited

U.S. PATENT DOCUMENTS

| | | | |
|---|---|---|---|
| 5,728,839 A | 3/1998 | Herrmann | |
| 6,426,419 B1 | 7/2002 | Grubbs et al. | |
| 6,552,139 B1 * | 4/2003 | Herrmann et al. | 526/171 |
| 6,787,620 B2 * | 9/2004 | Herrmann et al. | 526/171 |

FOREIGN PATENT DOCUMENTS

EP 0721953 7/1996
WO WO-97/06185 2/1997

OTHER PUBLICATIONS

Kocher, "Neue Wege zu N-heterocyclischen Carbenen und deren Metalkomplexen; Anwendungen in der Homogenkatalyse", Dissertation, Technische Universitat Munchen, 1997, Seiten 31-59; 124-147; 158-173.

Schattenmann, "Neue Katalysatoren fur die Olefin-Metathese", Dissertation an der Fakultat fur Chemie, Biologie und Geowissenschaft der TU Muchen, 1998, Seiten 157-240; & TU Jahrbuch 1997, Seite 580.

Weskamp, T. et al., Angew. Chem. Int. Ed. 37:2490-2493, "A Novel Class of Ruthenium Catalysts for Olefin Metathesis", 1998.

* cited by examiner

*Primary Examiner*—Porfirio Nazario-Gonzalez
(74) *Attorney, Agent, or Firm*—Connelly Bove Lodge & Hutz LLP

(57) ABSTRACT

The invention relates to a complex compound of ruthenium of the general structural formula I

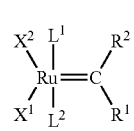

in which $X^1$ and $X^2$ may be identical or different and represent an anionic ligand,
in which $R^1$ and $R^2$ are identical or different, but may also have a ring,
in which $R^1$ and $R^2$ represent hydrogen or/and a hydrocarbon group,
in which the ligand $L^1$ is a N-heterocyclic carbene and in which the ligand $L^2$ is a neutral electron donor, especially a N-heterocyclic carbene or an amine, imine, phosphane, phosphite, stibine, arsine, carbonyl compound, carboxyl compound, nitrile, alcohol, ether, thiol or thioether,
wherein $R^1$, $R^2$, $R^3$ and $R^4$ represent hydrogen or/and hydrocarbon groups.

The invention relates also to a process for the preparation of acyclic olefins having two or more carbon atoms or/and of cyclic olefins having four or more carbon atoms from acyclic olefins having two or more carbon atoms or/and from cyclic olefins having four or more carbon atoms by olefin metathesis reaction in the presence of at least one catalyst, wherein such a complex compound is used as catalyst and wherein $R'^1$, $R'^2$, $R'^3$ and $R'^4$ hydrogen or/and hydrocarbon groups.

26 Claims, 2 Drawing Sheets

ALKYLIDENE COMPLEXES OF RUTHENIUM CONTAINING N-HETEROCYCLIC CARBENE LIGANDS; USE AS HIGHLY ACTIVE, SELECTIVE CATALYSTS FOR OLEFIN METATHESIS

RELATED APPLICATIONS

This application is a division of Ser. No. 10/630,552, filed Jul. 29, 2003, which is a division of Ser. No. 09/647,742, filed Nov. 27, 2000, now U.S. Pat. No. 6,635,768, which is filed as a 371 of international application No. PCT/EP99/01785, filed on Mar. 18, 1999. This application claims benefit to German application no. 198 15 275.2 filed Apr. 6, 1998.

DESCRIPTION

Alkylidene complexes of ruthenium with N-heterocyclic carbene ligands and their use as highly active, selective catalysts for olefin metathesis.

The invention relates to alkylidene complex compounds of ruthenium with N-heterocyclic carbene ligands and to a process for the preparation of olefins by olefin metathesis from acyclic olefins having two or more carbon atoms or/and from cyclic olefins having four or more carbon atoms, wherein at least one of those alkylidene complex compounds is used as catalyst.

Transition-metal-catalyzed C—C linkages belong to the most important reactions of organic synthesis chemistry. Olefin metathesis constitutes an important element in this connection, because it is possible by means of that reaction to synthesize olefins that are free of by-products. Olefin metathesis has high potential not only in the field of preparative organic synthesis (RCM, ethenolysis, metathesis of acylic olefins), but also in polymer chemistry (ROMP, ADMET, alkyne polymerization). Since its discovery in the 1950s, it has been possible to implement several large-scale processes. Nevertheless, olefin metathesis has only recently advanced to a widely applicable synthesis method owing to the discovery of new catalysts (J. C. Mol in: B. Cornils, W. A. Herrmann: Applied Homogeneous Catalysis with Organometallic Compounds, VCH, Weinheim, 1996, p. 318-332; M. Schuster, S. Blechert, Angew. Chem. 1997, 109, 2124-2144; Angew. Chem. Int. Ed. Engl. 1997, 36, 2036-2056).

Numerous standard works have made a substantial contribution towards the understanding of such transition-metal-catalyzed reactions, in which an exchange of alkylidene units between olefins takes place. The generally accepted mechanism contains metal alkylidene complexes as the active species. These react with olefins to form metallacyclobutane intermediates, which generate olefins and alkylidene complexes again by cycloreversion. The isolation of metathesis-active alkylidene and metallacyclobutane complexes substantiates these mechanistic ideas.

Many examples are found primarily in the complex chemistry of molybdenum and tungsten. Schrock's works in particular have yielded well-defined alkylidene complexes which are controllable in terms of their reactivity (J. S. Murdzek, R. R. Schrock, Organometallics 1987, 6, 1373-1374). The introduction of a chiral ligand sphere into such complexes enabled the synthesis of polymers having high tacticity (K. M. Totland, T. J. Boyd, G. C. Lavoie, W. M. Davis, R. R. Schrock, Macromolecules 1996, 29, 6114-6125). Chiral complexes of the same structural type have also been used successfully in ring-closing metathesis (O. Fujimura, F. J. d. I. Mata, R. H. Grubbs, Organometallics 1996, 15, 1865-1871). However, high sensitivity towards functional groups, air and water is found to be a disadvantage.

Phosphane-containing complex systems of ruthenium have recently become established (R. H. Grubbs, S. T. Nguyen, L. K. Johnson, M. A. Hillmyer, G. C. Fu, WO 96/04289, 1994; P. Schwab, M. B. France, J. W. Ziller, R. H. Grubbs, Angew. Chem. 1995, 107, 2179-2181; Angew. Chem. Int. Ed. Engl. 1995, 34, 2039-2041). Owing to the electron-rich, "soft" nature of later transition metals, such complexes have high tolerance towards hard, functional groups. This is demonstrated, for example, by their use in the chemistry of natural substances (RCM of dienes) (Z. Yang, Y. He, D. Vourloumis, H. Vallberg, K. C. Nicolaou, Angew. Chem. 1997, 109, 170-172; Angew. Chem., Int. Ed. Engl. 1997, 36, 166-168; D. Meng, P. Bertinato, A. Balog, D. S. Su, T. Kamenecka, E. J. Sorensen, S. J. Danishefsky, J. Am. Chem. Soc. 1997, 119, 2733-2734; D. Schinzer, A. Limberg, A. Bauer, O. M. Böhm, M. Cordes, Angew. Chem. 1997, 109, 543-544; Angew. Chem., Int. Ed. Engl. 1997, 36, 523-524; A. Fürstner, K. Langemann, J. Am. Chem. Soc. 1997, 119, 9130-9136).

However, the range of variation of the phosphane ligands used is very limited on account of steric and electronic factors. Only strongly basic, sterically demanding alkylphosphanes such as tricyclohexyl-, triisopropyl- and tricyclopentyl-phosphane are suitable for the metathesis of acyclic olefins and slightly strained ring systems. Accordingly, such catalysts cannot be adjusted in terms of their reactivity. Nor has it been possible to produce chiral complexes of that structural type.

For those reasons, the object was to develop tailored metathesis catalysts which are distinguished by a variable ligand sphere as well as by high tolerance towards functional groups, and which allow fine adjustment of the catalyst for specific properties of different olefins. A further object was to provide a process for the preparation of olefins, in which process the reactivity is adjustable and chiral complexes can be produced.

The object is achieved according to the invention by a complex compound of ruthenium of the general structural formula I

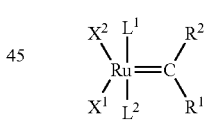

in which $X^1$ and $X^2$, which may be identical or different, represent an anionic ligand, in which $R^1$ and $R^2$ are identical or different, but may also have a ring, in which $R^1$ and $R^2$ represent hydrogen or/and a hydrocarbon group, wherein the hydrocarbon groups, which may be identical or different, consist of straight-chain, branched, cyclic or/and non-cyclic radicals from the group alkyl radicals having from 1 to 50 carbon atoms, alkenyl radicals having from 1 to 50 carbon atoms, alkynyl radicals having from 1 to 50 carbon atoms, aryl radicals having from 1 to 30 carbon atoms and silyl radicals, wherein the hydrogen atoms in the hydrocarbon or/and silyl groups may be replaced partially or wholly by one or more identical or different groups alkyl, aryl, alkenyl, alkynyl, metallocenyl, halogen, nitro, nitroso, hydroxy, alkoxy, aryloxy, amino, amido, carboxyl, carbonyl, thio or/and sulfonyl, in which the ligand $L^1$ is a N-heterocyclic carbene of the general formulae II-V and in which the ligand $L^2$ is a neutral electron donor, especially a N-heterocyclic carbene of the general formulae II-V or an amine, imine, phosphane, phosphite, stibine, arsine, carbonyl compound, carboxyl compound, nitrile, alcohol, ether, thiol or thioether,

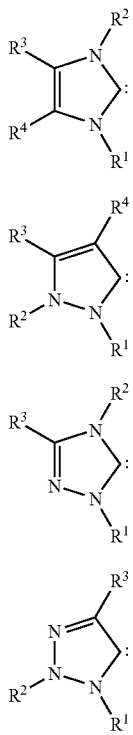

wherein $R^1$, $R^2$, $R^3$ and $R^4$ in formulae II, III, IV and V may be identical or different and represent hydrogen or/and hydrocarbon groups, wherein the hydrocarbon groups consist of identical or different, cyclic, non-cyclic, straight-chain or/and branched radicals from the group alkyl radicals having from 1 to 50 carbon atoms, alkenyl radicals having from 1 to 50 carbon atoms, alkynyl radicals having from 1 to 50 carbon atoms and aryl radicals having from 1 to 30 carbon atoms, in which at least one hydrogen may optionally be replaced by functional groups, and wherein $R^3$ and $R^4$ may optionally represent one or more identical or different groups halogen, nitro, nitroso, alkoxy, aryloxy, amido, carboxyl, carbonyl, thio or/and sulfonyl.

Figure 1:
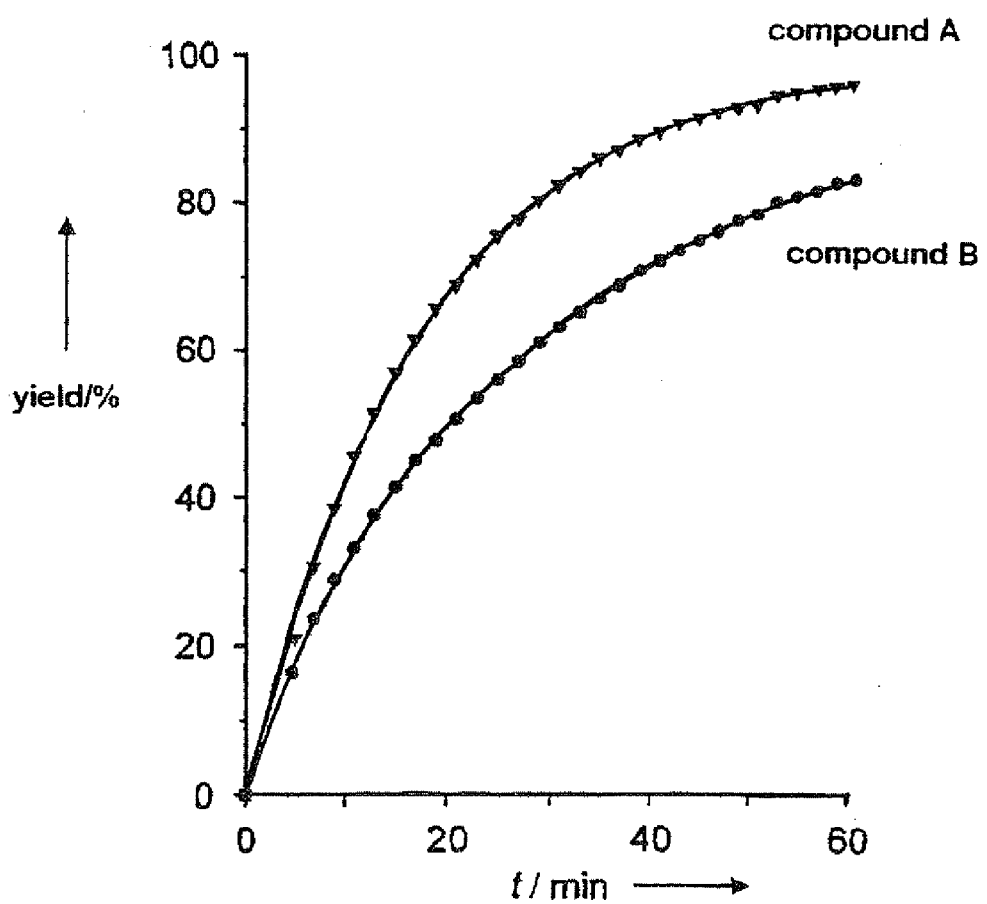
FIG. 1 illustrates the yield % versus t/min for compounds A and B in a ring-opening metathesis polymerization of 1,5-cyclooctadiene
Figure 2:
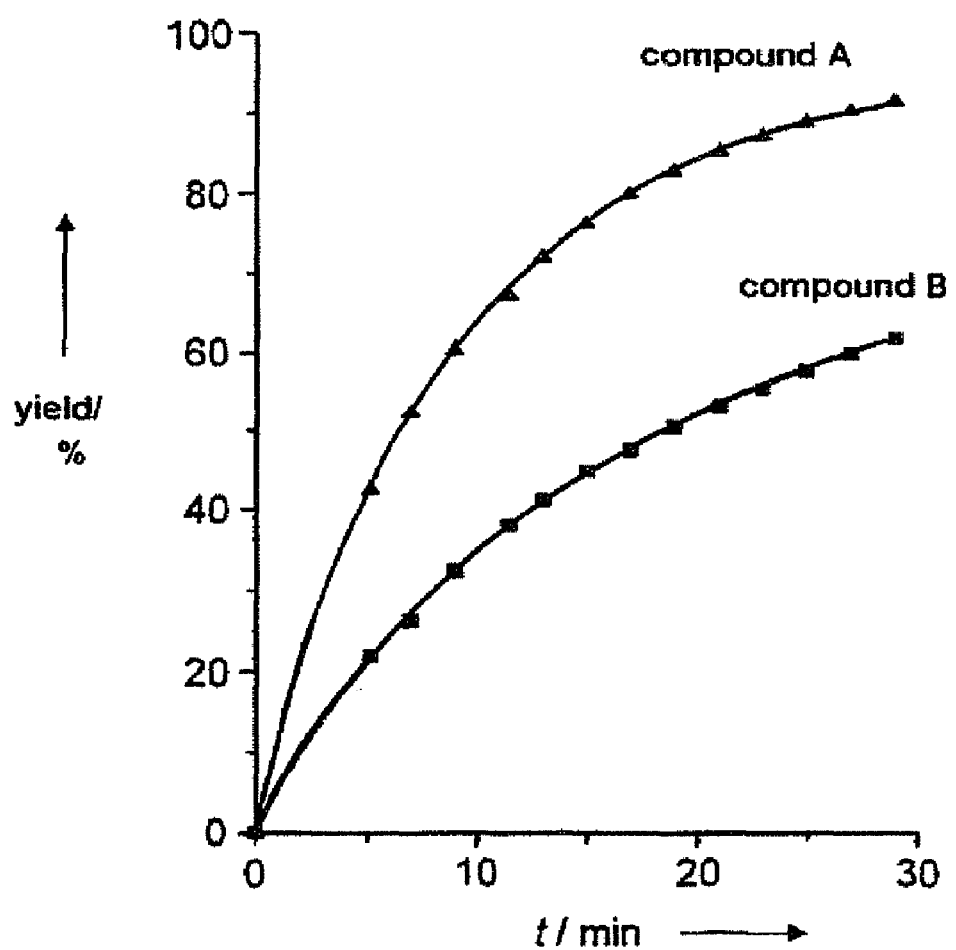
FIG. 2 illustrates the yield % versus t/min for compounds A and B in a ring-opening metathesis polymerization of cyclooctene.

The complex compounds according to the invention are highly active catalysts for olefin metathesis. They are particularly inexpensive. Olefin metathesis using the catalysts according to the invention is distinguished by their great variety in the ligand sphere as well as by high tolerance towards very different functional groups. By varying the N-heterocyclic carbene ligands, which are readily accessible in terms of preparation, the activity and selectivity can be controlled in a targeted manner and, moreover, chirality can be introduced in a simple manner.

The anionic ligands $X^1$ and $X^2$ of the complex compound according to the invention may be identical or different and are preferably halide, pseudohalide, tetraphenyl borate, perhalogenated tetraphenyl borate, tetrahaloborate, hexahalophosphate, hexahaloantimonate, trihalomethane-sulfonate, alkoxide, carboxylate, tetrahaloaluminate, tetracarboxyl cobaltate, hexahaloferrate(III), tetrahaloferrate(III) or/and tetrahalopalladate(II), wherein halide, pseudohalide, tetraphenyl borate, perfluorinated tetra-phenyl borate, tetrafluoroborate, hexafluorophosphate, hexafluoroantimonate, trifluoromethanesulfonate, alkoxide, carboxylate, tetrachloroaluminate, tetracarboxyl cobaltate, hexafluoroferrate(III), tetrachloroferrate(III) or/and tetrachloropalladate(II) are preferred and wherein, of the pseudohalides, preference is given to cyanide, rhodanide, cyanate, isocyanate, thiocyanate and isothiocyanate.

In the general formulae II, III, IV and V, the hydrogen in the hydrocarbon groups $R^1$, $R^2$, $R^3$ and $R^4$ may be replaced partially or wholly by one or more identical or different groups halogen, nitro, nitroso, hydroxy, alkoxy, aryloxy, amino, amido, carboxyl, carbonyl, thio, sulfonyl or/and metallocenyl. In those formulae, $R^3$ and $R^4$ may represent a fused ring system.

The ligands $L^1$ and $L^2$ of the complex compound of the general structural formula I may form a chelate ligand of the general formula VI

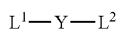

wherein the bridging members designated Y may consist of cyclic, non-cyclic, straight-chain or/and branched radicals from the group alkylene radicals having from 1 to 50 carbon atoms, alkenylene radicals having from 1 to 50 carbon atoms, alkynylene radicals having from 1 to 50 carbon atoms, arylene radicals having from 1 to 30 carbon atoms, metallocenylene, borylene and silylene radicals, in which at least one hydrogen may optionally be substituted by one or more identical or different groups alkyl, aryl, alkenyl, alkynyl, metallocenyl, halogen, nitro, nitroso, hydroxo, alkoxy, aryloxy, amino, amido, carboxyl, carbonyl, thio or/and sulfonyl, preferably by alkyl, aryl or/and metallocenyl.

The alkyl radicals, alkenyl radicals, alkynyl radicals, or the alkylene radicals, alkenylene radicals, alkynylene radicals, in formulae I to VII preferably have from 1 to 20 carbon atoms, particularly preferably from 1 to 12 carbon atoms.

The ligands of the general formulae II, III, IV, V or/and VI may have central, axial or/and planar chirality.

In the general structural formula I of the complex compound, $R^1$ to $R^2$ preferably represent hydrogen, substituted or/and unsubstituted alkyl, alkenyl or/and aryl radicals, $X^1$ and $X^2$ are preferably halide, alkoxide or/and carboxylate ions, and $L^1$ and $L^2$ preferably represent a N-heterocyclic carbene of the general formula II.

The synthesis of the complexes is usually carried out by ligand substitution of appropriate phosphane complexes. Those complexes may be selectively disubstituted according to reaction equation (1) or monosubstituted according to reaction equation (2). In the case of monosubstitution, the second phosphane may be selectively substituted by a different electron donor, e.g. pyridine, phosphane, N-heterocycle carbene, phosphite, stibine, arsine, according to reaction equation (3).

In that manner it is possible in particular to prepare for the first time chiral ruthenium-based catalysts having metathesis activity (complex examples 2 and 3).

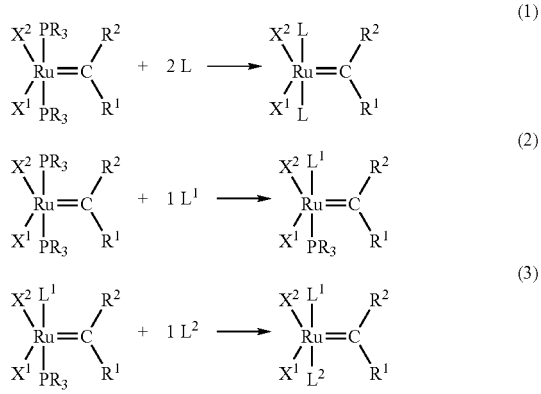

The complex compounds according to the invention prove to be extremely efficient catalysts in olefin metathesis. The excellent metathesis activity is demonstrated in the Examples by means of several examples of different metathesis reactions.

Accordingly, this invention also includes the processes of all olefin metathesis reactions, such as ring-opening metathesis polymerization (ROMP), metathesis of acyclic olefins, ethenolysis, ring-closing metathesis (RCM), acyclic diene metathesis polymerization (ADMET) and depolymerization of olefinic polymers. The high stability and tolerance of the complex compounds according to the invention towards functional groups, especially groups of alcohols, amines, thiols, ketones, aldehydes, carboxylic acids, esters, amides, ethers, silanes, sulfides and halogens, permits the presence of such functional groups during the metathesis reaction.

The object is further achieved by a process for the preparation of acyclic olefins having two or more carbon atoms or/and of cyclic olefins having four or more carbon atoms, in each case corresponding to the general formula VII

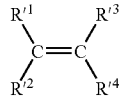

from acyclic olefins having two or more carbon atoms or/and from cyclic olefins having four or more carbon atoms, in each case corresponding to the general formula VII, by olefin metathesis reaction in the presence of at least one catalyst, wherein a catalyst as claimed in any one of claims 1 to 7 is used and $R^{r1}$, $R^{r2}$, $R^{r3}$ and $R^{r4}$ in the general formula VII represent hydrogen or/and hydrocarbon groups, wherein the hydrocarbon group consists of identical or different straight-chain, branched, cyclic or/and non-cyclic radicals from the group alkyl radicals having from 1 to 50 carbon atoms, alkenyl radicals having from 1 to 50 carbon atoms, alkynyl radicals having from 1 to 50 carbon atoms, aryl radicals having from 1 to 30 carbon atoms, metallocenyl or/and silyl radicals, in which at least one hydrogen may optionally be replaced by a functional group, wherein $R^{r1}$, $R^{r2}$, $R^{r3}$ and $R^{r4}$ optionally represent one or more identical or different groups halogen, nitro, nitroso, hydroxy, alkoxy, aryloxy, amino, amido, carboxyl, carbonyl, thio, sulfonyl or/and metallocenyl.

The olefins that are used or/and that are to be prepared preferably contain one or/and more than one double bond. One or more of $R^{r1}$, $R^{r2}$, $R^{r3}$ and $R^{r4}$, identical or different, in the olefins of the general formula VII, in pairs, especially form a ring. The hydrogen in the hydrocarbon groups $R^{r1}$, $R^{r2}$, $R^{r3}$ and $R^{r4}$ in the olefins of the general formula VII has preferably been replaced partially or wholly by one or more identical or different groups halogen, silyl, nitro, nitroso, hydroxy, alkoxy, aryloxy, amino, amido, carboxyl, carbonyl, thio, sulfonyl or/and metallocenyl.

In the process according to the invention, the process may be carried out with or without a solvent, but preferably with organic solvents. The process according to the invention can preferably be carried out with the addition of a Brönstedt acid, preferably HCl, HBr, HI, $HBF_4$, $HPF_6$ or/and trifluoroacetic acid, or/and with the addition of a Lewis acid, preferably $BF_3$, $AlCl_3$ or/and $ZnI_2$.

Surprisingly, it accordingly becomes possible for the first time to tailor the most varied olefins individually to different properties on the basis of a slight variation in the catalysis conditions or/and in the catalysts, because the process according to the invention for the preparation of olefins has unexpectedly high tolerance towards functional groups.

EXAMPLES

The Examples which follow illustrate the invention but do not limit the scope thereof.

1) Preparation of the Complex Compound According to the Invention

General Working Procedure:

1 mmol. of $(PPh_3)_2Cl_2Ru(=CHPh)$ was dissolved in 20 ml of toluene, and a solution of 2.2 equiv. of the appropriate imidazolin-2-ylidene in 5 ml of toluene was added thereto. The reaction solution was stirred for 45 minutes at room temperature RT and then concentrated to about 2 ml, and the crude product was precipitated with 25 ml of pentane. The crude product was taken up several times in 2 ml of toluene and precipitated with 25 ml of pentane. The residue was extracted with toluene, and the solution was concentrated to dryness, washed twice with pentane and dried for several hours under a high vacuum.

For characterization purposes, the data of low-temperature NMR spectra are for the most part given, because some of the spectra at room temperature do not contain all the information on account of dynamic effects.

The following compounds are prepared according to the indicated general working procedure:

1a) Benzylidene-dichloro-bis(1,3-diisopropylimidazolin-2-ylidene)-ruthenium—complex compound 1

Yield: 487 mg (0.86 mmol.=86% of theory)

Elemental analysis EA for $C_{25}H_{38}Cl_2N_4Ru$ (566.58): Found C, 53.21; H, 6.83; N, 9.94. calculated C, 53.00; H, 6.76; N, 9.89.

$^1$H-NMR ($CD_2Cl_2$/200 K): δ 20.33 (1H, s, Ru=CH), 8.25 (2H, d, $^3J_{HH}$=7.6 Hz, o-H of $C_6H_5$), 7.63 (1H, t, $^3J_{HH}$=7.6 Hz, p-H of $C_6H_5$), 7.34 (2H, t, m-H of $C_6H_5$, $^3J_{HH}$=7.6 Hz), 7.15 (2H, br, NCH), 7.03 (2H, br, NCH), 5.97 (2H, spt, $^3J_{HH}$=6.4 Hz, NCHMe$_2$), 3.73 (2H, spt, $^3J_{HH}$=6.4 Hz, NCHMe$_2$), 1.64 (12H, d, $^3J_{HH}$=6.4 Hz, NCHMe$_2$), 1.11 (6H, d, $^3J_{HH}$=6.4 Hz, NCHMe$_2$), 0.75 (6H, d, $^3J_{HH}$=6.4 Hz, NCHMe$_2$).

$^{13}$C-NMR (CD$_2$Cl$_2$/200 K): δ 295.6 (Ru=CH), 183.5 (NCN), 151.6 (ipso-C of C$_6$H$_5$), 129.5, 128.6 and 128.1 (o-C, m-C and p-C of C$_6$H$_5$), 118.1 and 117.2 (NCH), 52.1 and 50.1 (NCHMe$_2$), 24.5, 23.8, 23.8 and 22.4 (NCHMe$_2$).

1b) Benzylidene-dichloro-bis(1,3-di-((R)-1'-phenylethyl)-imidazolin-2-ylidene)-ruthenium—complex compound 2

Yield: 676 mg (0.83 mmol.=83% of theory)

EA for C$_{45}$H$_{46}$Cl$_2$N$_4$Ru (814.86): Found C, 66.48; H, 5.90; N, 6.73. calc. C, 66.33; H, 5.69; N 6.88.

$^1$H-NMR (CD$_2$Cl$_2$/200 K): δ 20.26 (1H, s, Ru=CH), 8.13 (2H, br, o-H C$_6$H$_5$), 7.78-6.67 (29H, of which 2m-H and 1p-H of C$_6$H$_5$, 20H of NCHMePh, 2H of NCHMePh and 4H of NCH), 4.91 (2H, m, NCHMePh), 1.84 (3H, d, $^3J_{HH}$=6.6 Hz, NCHMePh), 1.81 (3H, d, $^3J_{HH}$=6.6 Hz, NCHMePh), 1.51 (3H, d, $^3J_{HH}$=6.6 Hz, NCHMePh), 1.21 (3H, d, $^3J_{HH}$=6.6 Hz, NCHMePh).

$^{13}$C-NMR (CD$_2$Cl$_2$/200 K): δ 294.7 (Ru=CH), 186.0 and 185.6 (NCN), 151.2 (ipso-C of C$_6$H$_5$), 141.2, 140.3, 140.1 and 139.9 (ipso-C of NCHMePh), 133.1-125.9 (o-C, m-C, p-C of C$_6$H$_5$ and NCHMePh), 120.5, 119.9, 119.2 and 118.8 (NCH), 57.6, 57.4, 56.7 and 56.1 (NCHMePh), 22.2, 20.6, 20.4 and 20.3 (NCHMePh).

1c) Benzylidene-dichloro-bis(1,3-di((R)-1'-naphthylethyl)-imidazolin-2-ylidene)-ruthenium—complex compound 3

Yield: 792 mg (0.78 mmol.=78% of theory)

EA for C$_{61}$H$_{54}$Cl$_2$N$_4$Ru (1015.1): Found C, 72.34; H, 5.46; N, 5.45. calc. C, 72.18; H 5.36; N 5.52.

$^1$H-NMR (CD$_2$Cl$_2$/260 K): δ 20.90 (1H, s, Ru=CH), 8.99 (2H, br, o-H of C$_6$H$_5$), 8.2-5.6 (39H, of which 2m-H and 1p-H of C$_6$H$_5$, 28H of NCHMeNaph, 4H of NCH and 4H of NCHMeNaph), 2.5-0.8 (12H, m, NCHMeNaph).

$^{13}$C-NMR (CD$_2$Cl$_2$/260 K): δ 299.9 (Ru=CH), 187.2 and 184.7 (NCN), 152.0 (ipso-C of C$_6$H$_5$), 136.0-124.0 (o-C, m-C, p-C of C$_6$H$_5$ and NCHMeNaph), 121.7, 121.0, 119.9 and 118.9 (NCH), 56.7, 56.1, 55.0 and 54.7 (NCHMeNaph), 24.7, 24.3, 21.0 and 20.0 (NCHMeNaph).

Slight deviations from the general working procedure are necessary for the following complexes:

1d) (4-Chlorobenzylidene)-dichloro-bis(1,3-diisopropyl-imidazolin-2-ylidene)-ruthenium—complex compound 4

1 mmol. of (PPh$_3$)$_2$Cl$_2$Ru[=CH(p-C$_6$H$_4$Cl)] was used as starting material. The further procedure corresponded to the general working procedure.

Yield: 535 mg (0.89 mmol.=89% of theory)

EA for C$_{24}$H$_{38}$Cl$_3$N$_4$Ru (601.03): Found C, 48.13;H, 6.33; N 9.24. calc. C, 47.96;H, 6.37; N, 9.32.

$^1$H-NMR (CD$_2$Cl$_2$/200 K): δ 20.33 (1H, s, Ru=CH), 8.25 (2H, d, J$_{HH}$=7.6 Hz, o-H of C$_6$H$_4$Cl), 7.63 (1H, t, $^3J_{HH}$=7.6 Hz, m-H of C$_6$H$_4$Cl), 7.15 (2H, br, NCH), 7.03 (2H, br, NCH), 5.97 (2H, spt, $^3J_{HH}$=6.4 Hz, NCHMe$_2$), 3.73 (2H, spt, $^3J_{HH}$=6.4 Hz, NCHMe$_2$), 1.64 (12H, d, $^3J_{HH}$=6.4 Hz, NCHMe$_2$), 1.11 (6H, d, $^3J_{HH}$=6.4 Hz, NCHMe$_2$), 0.75 (6H, d, $^3J_{HH}$=6.4 Hz, NCHMe$_2$).

$^{13}$C-NMR (CD$_2$Cl$_2$/200 K): δ 295.6 (Ru=CH), 183.5 (NCN), 151.6 (ipso-C of C$_6$H$_4$Cl), 134.3 (p-C of C$_6$H$_4$Cl), 128.6 and 128.1 (o-C and m-C of C$_6$H$_4$Cl), 118.1 and 117.2 (NCH), 52.1 and 50.1 (NCHMe$_2$), 24.5, 23.8, 23.8 and 22.4 (NCHMe$_2$).

1e) Benzylidene-dichloro-bis(1,3-dicyclohexylimidazolin-2-ylidene)-ruthenium—complex compound 5

1 mmol. of (PPh$_3$)$_2$Cl$_2$Ru(=CHPh) was dissolved in 25 ml of toluene, and a solution of 2.2 equiv. of 1,3-dicyclohexyl-imidazolin-2-ylidene in 5 ml of toluene was added thereto. The reaction solution was stirred for 45 minutes at RT and then freed of solvent. Unlike in the general working procedure, the crude product was purified by flash chromatography.

Yield: 305 mg (0.42 mmol.=42% of theory)

EA for C$_{37}$H$_{54}$Cl$_2$N$_4$Ru (726.84): Found C, 61.23; H 7.56; N 7.87. calc. C, 61.14; H, 7.49; N 7.71.

$^1$H-NMR (CD$_2$Cl$_2$/298 K): δ 20.45 (1H, s, Ru=CH), 8.31 (2H, d, $^3J_{HH}$=7.6 Hz, o-H— of C$_6$H$_5$), 7.63 (1H, t, $^3J_{HH}$=7.6 Hz, p-H— of C$_6$H$_5$), 7.34 (2H, t, $^3J_{HH}$=7.6 Hz, m-H— of C$_6$H$_5$), 7.14 (2H, br, NCH), 7.00 (2H, br, NCH), 6.06 (2H, br, CH of NC$_6$H$_{11}$), 3.82 (2H, br, CH of NC$_6$H$_{11}$), 1.64 (12H, br, CH$_2$ of NC$_6$H$_{11}$), 0.93 (12H, br, CH$_2$ of NC$_6$H$_{11}$).

$^{13}$C-NMR (CD$_2$Cl$_2$/298 K): δ 299.4 (Ru=CH), 182.9 (NCN), 152.0 (ipso-C of C$_6$H$_5$), 131.1, 129.8 and 129.1 (o-C, m-C and p-C of C$_6$H$_5$), 118.3 and 117.8 (br, NCH), 59.6 and 57.5 (br, CH of NC$_6$H$_{11}$), 35.7, 26.9 and 25.6 (br, CH$_2$ of NC$_6$H$_{11}$).

1f) Benzylidene-dichloro-(1,3-di-tert.-butylimidazolin-2-ylidene)-(triphenylphosphine)-ruthenium—complex compound 6

1 mmol. of (PPh$_3$)$_2$Cl$_2$Ru(=CHPh) was dissolved in 20 ml of toluene, and a solution of 1.1 equiv. of 1,3-di-tert.-butyl-imidazolin-2-ylidene in 5 ml of toluene was added thereto. The reaction solution was stirred for 30 minutes at RT and then concentrated to about 2 ml, and the crude product was precipitated with 25 ml of pentane. Further working-up was carried out in accordance with the general working procedure.

Yield: 493 mg (0.70 mmol.=70% of theory)

EA for C$_{36}$H$_{41}$Cl$_2$N$_2$P$_1$Ru (704.69): Found C, 61.12; H, 5.55; N 3.62; P, 4.59. calc. C, 61.36; H, 5.86; N 3.98; P, 4.38.

$^1$H-NMR (CD$_2$Cl$_2$/200 K): δ 20.70 (1H, s, Ru=CH), 8.03 (2H, d, $^3J_{HH}$=7.6 Hz, o-H of C$_6$H$_5$), 7.50-6.95 (20H, of which 2m-H and 1p-H of C$_6$H$_5$, 15H of PPh$_3$ and 2H of NCH), 1.86 (9H, s, NCMe$_3$), 1.45 (9H, s, NCMe$_3$).

$^{13}$C-NMR (CD$_2$Cl$_2$/200 K): δ 307.4 (br, Ru=CH), 178.3 (d, J$_{PC}$=86 Hz, NCN), 151.5 (d, J$_{PC}$=4.5 Hz, ipso-C of C$_6$H$_5$), 135.0 (m, o-C of PPh$_3$), 131.9 (m, ipso-C of PPh$_3$), 130.2 (s, p-C of PPh$_3$), 129.5, 128.6 and 128.1 (s, o-C, m-C and p-C of C$_6$H$_5$), 128.0 (m, m-C of PPh$_3$), 117.7 and 117.6 (NCH), 58.7 and 58.5 (NCMe$_3$), 30.0 and 29.5 (NCMe$_3$).

$^{31}$P-NMR (CD$_2$Cl$_2$/200 K): δ 40.7 (s, PPh$_3$).

2) Use of the Complex Compound According to the Invention in Olefin Metathesis

The Examples given hereinbelow demonstrate the potential of the complex compounds according to the invention in olefin metathesis. The advantage of the complex compounds according to the invention compared with phosphane-containing complexes is that the radicals R on the nitrogen atoms of the N-heterocyclic carbene ligands can be varied in a targeted and inexpensive manner. By tailoring the catalysts according to the invention in that manner relative to individual properties of the olefins to be metathesized, the activity and the selectivity of the reaction can be controlled.

2a) Ring-opening Metathesis Polymerization (ROMP):

Norbornene, cyclooctene and functionalized norbornene derivatives are used as examples.

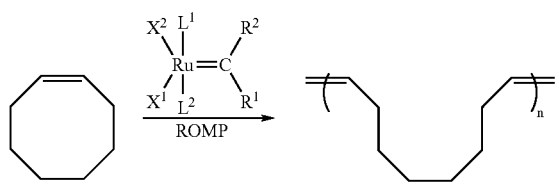

(4)

Typical Reaction Batch for the Polymerization of Cyclooctene (or Norbornene):

410 μl (3.13 mmol.) of cyclooctene were introduced into a solution of 3.6 mg (6.3 μmol.) of 1 in 0.5 ml of methylene chloride. After about 10 minutes, a highly viscous gel had formed, which could no longer be stirred. 1 ml of methylene chloride was added. This procedure was repeated whenever the stirrer ceased to perform (3 ml of methylene chloride in total). After 1 hour, 5 ml of methylene chloride were added, to which small amounts of tert.-butyl ether and 2,6-di-tert.-butyl-4-methylphenol had been added. After a further 10 minutes, the solution was slowly added dropwise to a large excess of methanol, and the whole was filtered and dried for several hours under a high vacuum.

Yield: 291 mg (2.64 mmol.=84.3% of theory)

TABLE 1

Polymerization of norbornene and cyclooctene

| Example | Complex | Monomer | Ratio [monomer]/[cat.] | Reaction time t | Yield |
|---|---|---|---|---|---|
| 2.1a | 1 | norbornene | 100:1 | 1 min | 91% |
| 2.1b | 5 | norbornene | 100:1 | 1 min | 92% |
| 2.1c | 1 | cyclooctene | 500:1 | 1 h | 84% |
| 2.1d | 1 | cyclooctene | 500:1 | 2 h | 97% |
| 2.1e | 5 | cyclooctene | 500:1 | 1 h | 87% |

Typical Reaction Batch for the Polymerization of Functionalized Norbornene Derivatives:

Formula VIII illustrates the basic structure of the norbornene derivatives used in Table 2.

VIII

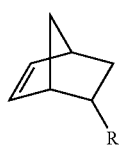

0.3 ml of a solution of 432 mg (3.13 mmol.) of 5-carboxylic acid 2-norbornene (formula VIII with R=CO$_2$H) in methylene chloride was added to a solution of 3.6 mg (6.3 μmol.) of 1 in 0.2 ml of methylene chloride. After about 10 minutes, a highly viscous gel had formed, which could no longer be stirred. A further 0.5 ml of methylene chloride was added. This procedure was repeated whenever the stirrer ceased to perform. After 1 hour, 5 ml of methylene chloride were added, to which small amounts of tert.-butyl ether and 2,6-di-tert.-butyl-4-methylphenol had been added. After a further 10 minutes, the solution was slowly added dropwise to a large excess of methanol, and the whole was filtered and dried for several hours under a high vacuum.

Yield: 423 mg (3.06 mmol.=98.1% of theory)

The reactions at 50° C. were carried out in an analogous manner in dichloroethane instead of methylene chloride.

TABLE 2

Polymerization of functionalized norbornene derivatives

| Example | Complex | Radical R in formula VIII | T [° C.] | Reaction time t | Yield |
|---|---|---|---|---|---|
| 2.1f | 1 | O$_2$CCH$_3$ | 25 | 30 min | 99% |
| 2.1g | 1 | CH$_2$OH | 25 | 2 h | 15% |
| 2.1h | 1 | CH$_2$OH | 50 | 2 h | 18% |
| 2.1i | 1 | CHO | 25 | 2 h | 36% |
| 2.1k | 1 | CHO | 50 | 2 h | 52% |
| 2.1l | 1 | COCH$_3$ | 25 | 2 h | 42% |
| 2.1m | 1 | COCH$_3$ | 50 | 2 h | 67% |
| 2.1n | 1 | CO$_2$H | 25 | 2 h | 98% |

The polymerization of norbornene took place within a period of seconds. In the cyclooctene polymerization, almost quantitative conversions were obtained within an hour (Table 1). Differences in respect of activity can be demonstrated by the use of different complexes under dilute conditions and show the dependence of the activity on the substitution pattern of the carbene ligands used. The high stability and tolerance towards functional groups is demonstrated by the polymerization of functionalized norbornene derivatives with esters, alcohol, aldehyde, ketone or/and carboxylic acid (Table 2). It has thereby been possible to polymerize monomers of the general formula VIII wherein R=CH$_2$OH, CHO and CO$_2$H for the first time.

2.2) Ring-closing Metathesis (RCM) of 1,7-octadiene:

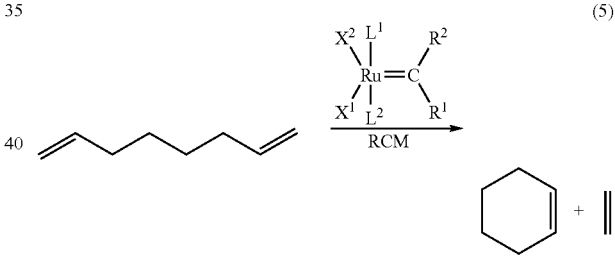

(5)

Typical Reaction Batch for the RCM of 1,7-octadiene:

46 μl (0.31 mmol.) of 1,7-octadiene were added to a solution of 3.6 mg (6.3 μmol.) of 1 in 2 ml of dichloro-ethane, and the reaction batch was placed in an oil bath at 60° C. After 1 hour, the reaction mixture was examined by GC/MS analysis.

TABLE 3

RCM of 1,7-octadiene (octadiene/catalyst = 50:1)

| Example | Complex | Solvent | T [° C.] | Reaction time t | Yield |
|---|---|---|---|---|---|
| 2.2a | 1 | methylene chloride | 25 | 5.5 h | 51% |
| 2.2b | 1 | methylene chloride | 25 | 24 h | 70% |
| 2.2c | 1 | dichloroethane | 60 | 1 h | 99% |
| 2.2d | 2 | dichloroethane | 60 | 1 h | 99% |
| 2.2e | 3 | dichloroethane | 60 | 1 h | 99% |
| 2.2f | 5 | dichloroethane | 60 | 1 h | 99% |

The potential in the ring-closing metathesis has been illustrated by the reaction of 1,7-octadiene to cyclohexene with the liberation of ethylene (Table 3). With 1, a yield of 51% was achieved after 5.5 hours; at 60° C., quantitative conversions were even achieved with all the complex compounds according to the invention which were used.

2.3) Metathesis of Acyclic Olefins

A) Metathesis of 1-octene:

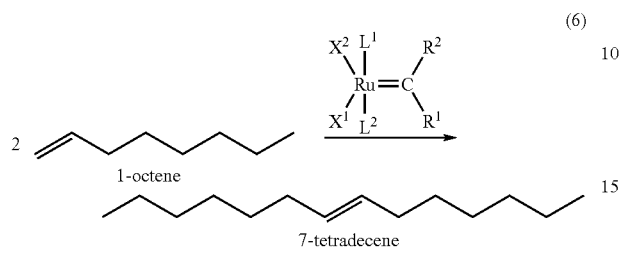

(6)

Typical Reaction Batch for the Metathesis of 1-octene:

49 µl (0.31 mmol.) of 1-octene were added to a solution of 3.6 mg (6.3 µmol.) of 1 in 2 ml of dichloroethane, and the reaction batch was placed in an oil bath at 60° C. After 3 hours, the reaction mixture was examined by GC/MS analysis.

TABLE 4

Homo-metathesis of 1-octene (octene/catalyst = 50:1)

| Example | Complex | T [° C.] | Reaction time t | Conversion of 1-octene | Selectivity[a] |
|---|---|---|---|---|---|
| 2.3a | 2 | 60 | 1 h | 31% | 98% |
| 2.3b | 2 | 60 | 2 h | 58% | 97% |
| 2.3c | 1 | 60 | 1 h | 83% | 73% |
| 2.3d | 1 | 60 | 3 h | 97% | 63% |

[a]The selectivity indicates the proportion of 7-tetradecene compared with other metathesis products B) Metathesis of Methyl Oleate:

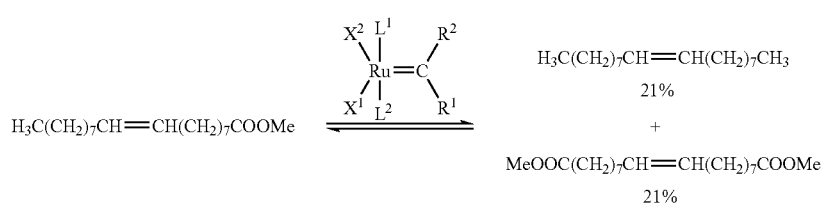

Typical Reaction Batch for the Metathesis of Methyl Oleate:

1.06 ml (3.13 mmol.) of methyl oleate were added to a solution of 3.6 mg (6.3 µmol.) of 1 in 0.5 ml of dichloroethane, and the reaction batch was placed in an oil bath at 60° C. for 15 hours. GC/MS analysis yielded the equilibrium of metathesis products shown in reaction equation (7).

The metathesis of terminal and internal olefins has been demonstrated by the homo-metathesis of 1-octene and methyl oleate. In the metathesis of methyl oleate as a natural raw material, the thermodynamic equilibrium can almost be reached within a period of 15 hours with catalyst 1 at an olefin:catalyst ratio of 500:1. In the metathesis of 1-octene, 7-tetradecene was not obtained as the only reaction product in all cases. An isomerization, detected by NMR spectroscopy, of 1-octene to 2-octene and subsequent olefin metathesis is responsible for that situation. Homo- and cross-metathesis of 1-octene and 2-octene yielded, in addition to 7-tetradecene, also 6-tridecene as the most frequent by-product, and small amounts of 6-dodecene, 1-heptene and 2-nonene. The product distribution is greatly dependent on the catalyst used. In the case of 2, 7-tetradecene was obtained almost selectively; the more active complex 1, on the other hand, yielded 7-tetradecene with a selectivity of only 63%, at a high conversion. 6-Tridecene was obtained as the principal by-product of the cross-metathesis of 1-octene with 2-octene.

What is claimed is:

1. A complex of ruthenium of the structural formula I,

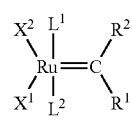

I where $X^1$ and $X^2$ are identical or different and are each an anionic ligand, $R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having from up to 30 carbon atoms and silyl radicals, or $R^1$ and $R^2$ form a ring, where one or more of the hydrogen atoms in the hydrocarbon or silyl groups or both the hydrocarbon and silyl group can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or sulfonyl groups, the ligand $L^1$ is an N-heterocyclic carbene of the formula II (7)

and the ligand $L^2$ is an amine, imine, phosphine, phosphite, stibine, arsine, carbonyl compound, carboxyl compound, nitrile, alcohol, ether, thiol or thioether

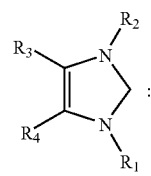

II where $R_1$, $R_2$, $R_3$ and $R_4$ in formula II are identical or different and are each hydrogen or a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having up to 50 carbon atoms, alkynyl radicals having up to 50 carbon atoms and aryl radicals having up to 30 carbon atoms, in which at least one hydrogen may be replaced by functional groups, and where one or both of $R_3$ and $R_4$ may be identical or different halogen, nitro, nitroso, alkoxy, aryloxy, amido, carboxyl, carbonyl, thio or sulfonyl groups.

2. A complex as claimed in claim 1, wherein $X^1$ and $X^2$ are identical or different and are each halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate (III) or tetrahalopalladate (II).

3. A complex as claimed in claim 1, wherein $R_3$ and $R_4$ in the formula II form a fused-on ring system.

4. A complex as claimed in claim 1, wherein $L^1$ and $L^2$ form a chelating ligand of the formula VI

   VI where the bridges Y comprise cyclic, noncyclic, straight-chain or branched radicals selected from the group consisting of alkylene radicals having up to 50 carbon atoms, alkenylene radicals having up to 50 carbon atoms, alkynylene radicals having up to 50 carbon atoms, arylene radicals having up to 30 carbon atoms, metallocenylene, borylene and silylene radicals in which one or more hydrogens may be replaced independently by identical or different alkyl, aryl, alkenyl, alkynyl, metallocenyl, halo, nitro, nitroso, hydroxy, alkoxy, aryloxy, amino, amido, carboxyl, carbonyl, thio or sulfonyl groups.

5. A complex as claimed in claim 4, wherein the ligands of the formula II, or VI have central, axial or planar chirality.

6. A complex as claimed in claim 1, wherein $R^1$ and $R^2$ in the structural formula I are independently hydrogen, substituted or unsubstituted alkyl, alkenyl or aryl radicals, $X^1$ and $X^2$ independently are halide, alkoxide or carboxylate ions and $L^1$ and $L^2$ are each an N-heterocyclic carbene of the formula II.

7. A process for preparing acyclic olefins having two or more carbon atoms or cyclic olefins having four or more carbon atoms, in each case of the formula VII

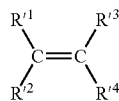   VII from acyclic olefins having two or more carbon atoms or from cyclic olefins having four or more carbon atoms, in each case corresponding to the formula VII by an olefin metathesis reaction in the presence of at least one catalyst comprising the complex as claimed in claim 1 and $R'^1$, $R'^2$, $R'^3$ and $R'^4$ in the formula VII are hydrogen or hydrocarbon groups, where the hydrocarbon groups are each selected independently from among straight-chain, branched, cyclic or noncyclic radicals of the group consisting of alkyl radicals having from 1 to 50 carbon atoms, alkenyl radicals having up to 50 carbon atoms, alkynyl radicals having up to 50 carbon atoms, aryl radicals having up to 30 carbon atoms, metallocenyl or silyl radicals, in which one or more hydrogens may be replaced by a functional group, where one or more of $R'^1$, $R'^2$, $R'^3$ and $R'^4$ may independently be identical or different halogen, nitro, nitroso, hydroxy, alkoxy, aryloxy, amino, amido, carboxyl, carbonyl, thio, sulfonyl or metallocenyl groups.

8. The process as claimed in claim 7, wherein one or more double bonds are present in the olefins used.

9. The process as claimed in claim 7, wherein $R'^1$, $R'^2$, $R'^3$ and $R'^4$ in the olefins of the formula VII to be prepared form, in pairs, one or more identical or different rings.

10. The process as claimed in claim 7, wherein some or all of the hydrogen atoms in the hydrocarbon groups $R'^1$, $R'^2$, $R'^3$ and $R'^4$ of the olefins of the formula VII to be prepared are replaced independently by identical or different halogen, silyl, nitro, nitroso, hydroxy, alkoxy, aryloxy, amino, amido, carboxyl, carbonyl, thio, sulfonyl or metallocenyl groups.

11. A method for synthesizing the compound as claimed in claim 1, comprising contacting a compound of the formula II

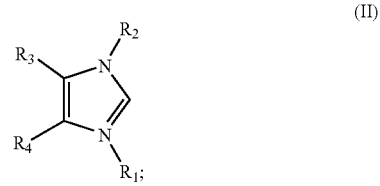   (II)

with a compound of the formula (I)

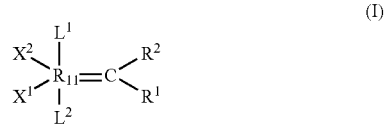   (I)

wherein:

$X^1$ and $X^2$ are either the same or different and are an anionic ligand;

$R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having up to 30 carbon atoms and silyl radicals, or $R^1$ and $R^2$ form a ring, $L^1$ and $L^2$ are either the same or different and are neutral electron donors;

where $R_1$, $R_2$, $R_3$ and $R_4$ in the formula II are identical or different and are each hydrogen or a hydrocarbon group, where the hydrocarbon groups are each selected independently from among straight-chain, branched, cyclic or noncyclic radicals of the group consisting of alkyl radicals having from 1 to 50 carbon atoms, alkenyl radicals having up to 50 carbon atoms, alkynyl radicals having up to 50 carbon atoms, aryl radicals having up to 30 carbon atoms, metallocenyl or silyl radicals, in which one or more hydrogens may be replaced by a functional group.

12. The method of claim 11, wherein $X^1$ and $X^2$ are each identical or different and are halide, pseudohalide, tetraphenylborate, perfluorinated tetraphenylborate, tetrafluoroborate, hexafluorophosphate, hexafluoroantimonate, trifluoromethanesulfonate, alkoxide, carboxylate, tetrachloroaluminate, tetracarbonylcobaltate, hexafluoroferrate (III), tetrachloroferrate (III) or tetrachloropalladate (II) and $L^1$ and $L^2$ are each independently selected from the group consisting of phosphine.

13. The method of claim 11, wherein $X^1$ and $X^2$ are each chloride and $L^1$ and $L^2$ are each independently selected from the group consisting of $P(cyclohexyl)_3$, $P(cyclopentyl)_3$, $P(isopropyl)_3$, and $P(phenyl)_3$.

14. The method of claim 11, wherein in formula (II), $R_1$ and $R_2$ are identical or different and are aryl, $R_3$ and $R_4$ are hydrogen.

15. The method of claim 11, wherein $R^1$ of formula (I) is hydrogen, $R^2$ is phenyl, or $R^1$ and $R^2$ of the formula (I) form a ring and $L^1$ is $P(phenyl)_3$ or $P(cyclohexyl)_3$, and $X^1$ and $X^2$ are each chloride.

16. In a process for olefin metathesis reaction wherein the improvement comprises using a catalyst which comprises the complex as claimed in claim 1.

17. An olefin metathesis process which comprises reacting an olefin with at least one double bond in the presence of a catalyst wherein said catalyst comprises the complex as claimed in claim 1.

18. A process for ring-opening metathesis polymer which comprises reacting an olefin with at least one double bond in the presence of a catalyst wherein said catalyst comprises the complex as claimed in claim 1.

19. A process for ring-closing metathesis which comprises reacting an olefin with at least one double bond in the presence of a catalyst wherein said catalyst comprises the complex as claimed in claim 1.

20. A process for acyclic diene metathesis polymerization which comprises reacting an olefin with at least one double bond in the presence of a catalyst wherein said catalyst comprises the complex as claimed in claim 1.

21. A process for depolymerization of an olefin polymer which comprises reacting an olefin with at least one double bond in the presence of a catalyst wherein said catalyst comprises the complex as claimed in claim 1.

22. The complex as claimed in claim 1, wherein in formula (II), $R^1$ and $R^2$ are aryl, and $R^3$ and $R^4$ are hydrogen.

23. The complex as claimed in claim 1, wherein $X^1$ and $X^2$ are halide.

24. The complex as claimed in claim 22, wherein $X^1$ and $X^2$ are Cl.

25. The complex as claimed in claim 24, wherein $L^2$ is $P(phenyl)_3$ or $P(cyclohexyl)_3$.

26. The complex as claimed in claim 24, wherein $R^1$ and $R^2$ in formula I together form a ring.

* * * * *